(12) United States Patent
Metzger et al.

(10) Patent No.: US 6,193,960 B1
(45) Date of Patent: Feb. 27, 2001

(54) TRIAZINE DERIVATIVES

(75) Inventors: Georges Metzger, Moernach (FR); Dieter Reinehr, Kandern; Helmut Luther, Grenzach-Wyhlen, both of (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/544,852

(22) Filed: Apr. 6, 2000

Related U.S. Application Data

(62) Division of application No. 09/231,152, filed on Jan. 15, 1999, now abandoned, which is a continuation of application No. 08/888,940, filed on Jul. 7, 1997, now abandoned.

(30) Foreign Application Priority Data

Jul. 8, 1996 (CH) .................................................. 1706/96

(51) Int. Cl.⁷ .............................. A61K 7/42; A61K 7/44; A61K 7/00; A61K 31/53
(52) U.S. Cl. ............................ 424/59; 424/60; 424/400; 424/401; 514/241
(58) Field of Search ............................. 424/59, 60, 400, 424/401; 514/241

(56) References Cited

U.S. PATENT DOCUMENTS

| | | | |
|---|---|---|---|
| 3,769,082 | 10/1973 | Roth | 260/246.6 |
| 4,617,390 | 10/1986 | Hoppe et al. | 544/197 |
| 4,650,867 | 3/1987 | Ronco et al. | 544/197 |
| 4,656,272 | 4/1987 | Martin et al. | 544/197 |
| 4,724,137 | 2/1988 | Hoppe et al. | 424/59 |
| 4,794,134 | 12/1988 | Wheeler et al. | 544/197 |
| 4,839,188 | 6/1989 | Wheeler et al. | 426/545 |
| 4,886,518 | 12/1989 | Sire | 8/566 |
| 5,120,844 | 6/1992 | Wheeler et al. | 544/209 |
| 5,801,244 | 9/1998 | Rapanti | 544/197 |

FOREIGN PATENT DOCUMENTS

| | | |
|---|---|---|
| 1017616 | 10/1957 | (DE) . |
| 0087098 | 8/1983 | (EP) . |
| 0196275 | 10/1986 | (EP) . |
| 0202611 | 11/1986 | (EP) . |
| 0305190 | 3/1989 | (EP) . |
| 0517104 | 12/1992 | (EP) . |
| 0570838 | 11/1993 | (EP) . |
| 0570845 | 11/1993 | (EP) . |

OTHER PUBLICATIONS

Unishi et al., Nippon Kagaku Kaishi. 4, pp. 565–568, Chem. Abstr. 95:25685, (1981).
Ganguly et al., J. Inst. Chem. (India), 68(1), pp. 17–18, Chem.. Abstr. 126:8080 (1996).

*Primary Examiner*—Shelley A. Dodson
(74) *Attorney, Agent, or Firm*—Kevin T. Mansfield

(57) ABSTRACT

The present invention relates to novel s-triazine compounds, processes for their preparation and the use of these novel compounds as UV filters in sunscreen compositions.

The novel compounds are those of the formula (1)

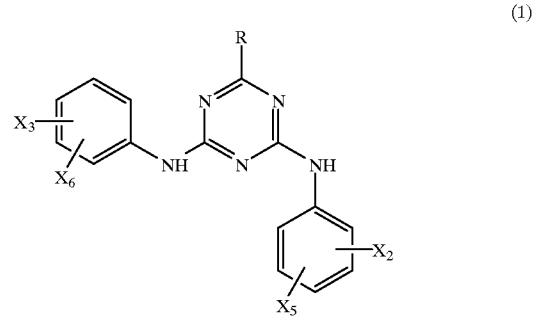

The triazine compounds of the formula (1) according to the invention are distinguished by a high UV absorption and are particularly suitable as UV filters, i.e. for protecting ultra-violet-sensitive organic materials, in particular the skin and the hair of man and animals, from the harmful action of UV radiation.

15 Claims, No Drawings

TRIAZINE DERIVATIVES

This is a divisional of application Ser. No. 09/231,152, filed on Jan. 15, 1999, now abandoned, which is a continuation of application Ser. No. 08/888,940, filed on Jul. 7, 1997, now abandoned.

The present invention relates to novel s-triazine compounds, processes for their preparation and the use of these novel compounds as UV filters in cosmetic compositions, in particular sunscreen compositions.

The novel s-triazine compounds are those of the formula

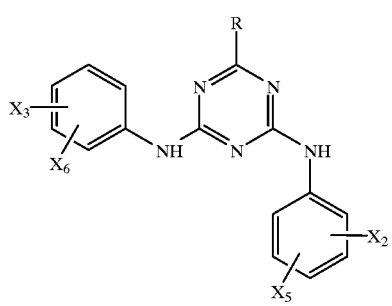

(1)

in which

R is halogen; straight-chain or branched $C_1$–$C_{22}$-Alkyl; straight-chain or branched $C_1$–$C_{22}$-Alkoxy; straight-chain or branched $C_1$–$C_{22}$-Hydroxyalkoxy; straight-chain or branched $C_1$–$C_{22}$-Alkoxyalkyl; —$NHR_1$;

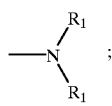

or a radical of the formula

(1a)

$X_1$, $X_2$ and $X_3$ independently of one another are —$CONHR_1$;

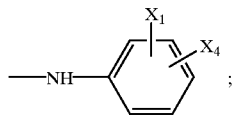

—$SO_2R_4$; —CN;

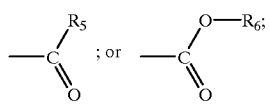

$R_1$ is hydrogen; straight-chain or branched $C_1$–$C_{22}$alkyl; $C_6$–$C_{12}$aryl which is unsubstituted, monosubstituted or polysubstituted by $C_1$–$C_4$alkyl; $C_7$–$C_{10}$aralkyl which is unsubstituted, monosubstituted or polysubstituted by $C_1$–$C_4$alkyl; $C_5$–$C_8$cycloalkyl; or a radical of the formula

(1b)

in which $A_1$ is straight-chain or branched $C_1$–$C_8$alkyl; $C_5$–$C_8$-cycloalkyl; $C_6$–$C_{12}$aryl which is unsubstituted, monosubstituted or polysubstituted by $C_1$–$C_4$alkyl; $C_7$–$C_{10}$aralkyl which is unsubstituted, monosubstituted or polysubstituted by $C_1$–$C_4$alkyl; and $m_1$ is 1 to 10;

$R_2$ and $R_3$ independently of one another are hydrogen; straight-chain or branched $C_1$–$C_{22}$alkyl; $C_5$–$C_8$cycloalkyl; $C_6$–$C_{12}$aryl which is unsubstituted, monosubstituted or polysubstituted by $C_1$–$C_4$alkyl; $C_7$–$C_{10}$aralkyl which is unsubstituted, monosubstituted or polysubstituted by $C_1$–$C_4$alkyl; a radical of the formula (1b); or a radical of the formula

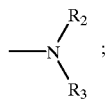

(1c)

$R_4$ is branched or straight-chain $C_1$–$C_{22}$alkyl; $C_5$–$C_8$cycloalkyl; $C_6$–$C_{12}$aryl which is unsubstituted, monosubstituted or polysubstituted by $C_1$–$C_4$alkyl; $C_7$–$C_{10}$aralkyl which is unsubstituted, monosubstituted or polysubstituted by $C_1$–$C_4$alkyl; a radical of the formula (1b); or

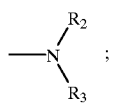

$R_5$ and $R_6$ independently of one another are hydrogen; straight-chain or branched $C_1$–$C_{22}$alkyl; $C_5$–$C_8$cycloalkyl; $C_6$–$C_{12}$aryl which is unsubstituted, monosubstituted or polysubstituted by $C_1$–$C_4$alkyl; $C_7$–$C_{10}$aralkyl which is unsubstituted, monosubstituted or polysubstituted by $C_1$–$C_4$alkyl; or a radical of the formula (1b);

$X_4$, $X_5$ and $X_6$ are hydrogen; or hydroxy;

where compounds of the formula (1) are not additionally included in which $X_1$ and $X_2$ are —$CONHR_1$; and $X_3$ is then

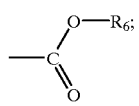

or compounds in which $X_1$ and $X_2$ are

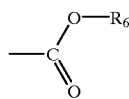

and $X_3$ is —CONHR$_1$; or compounds in which $X_1$, $X_2$ and $X_3$ are

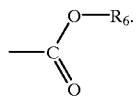

Straight-chain and branched $C_1$–$C_{22}$alkyl are, for example, methyl, ethyl, propyl, isopropyl, n-butyl, sec-butyl, isobutyl, t-butyl, 2-ethylbutyl, n-pentyl, isopentyl, 1-methylpentyl, 1,3-di-methylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl or eicosyl.

Examples of straight-chain and branched $C_1$–$C_{22}$alkoxy are methoxy, ethoxy, propoxy, isopropoxy, butoxy, isobutoxy, sec-butoxy, tert-butoxy, pentoxy, isopentoxy, n-heptyloxy, n-octyloxy, isooctyloxy, n-nonyloxy, isononyloxy, decyloxy, n-dodecyloxy, pentadecyloxy; heptadecyloxy, octadecyloxy or eicosyloxy.

$C_5$–$C_8$-Cycloalkyl is, for example, cyclopentyl, cycloheptyl, cyclooctyl and in particular cyclohexyl.

Examples of $C_6$–$C_{12}$aryl which may be mentioned in particular are phenyl, naphthyl and biphenylyl.

Examples of $C_7$–$C_{10}$aralkyl are benzyl, phenethyl, α-methylphenethyl or α,α-dimethylbenzyl.

"Alkylene" in the formula (1b) is a bivalent alkylene group having 2 to 5, preferably 2 to 4, carbon atoms. It is in this case preferably the —CH$_2$—CH$_2$—; —CH$_2$CH$_2$CH$_2$—; —CH$_2$—CH$_2$—CH$_2$—;

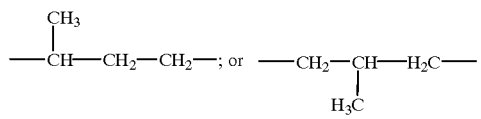

group. Among these alkylene groups, the —CH$_2$—CH$_2$— and the

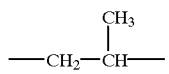

groups are very particularly preferred.

Halogen is fluorine, bromine or preferably chlorine.

Preferred triazine compounds are those of the formula (2)

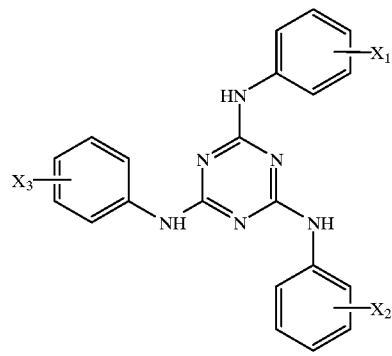

$X_1$, $X_2$ and $X_3$ are as defined for formula (1).

Predominant triazine compounds are those of the formula (1), in which $X_1$, $X_2$ and $X_3$ are in the ortho-position to the phenylamino radical of the triazine, i.e. compounds of the formula (3)

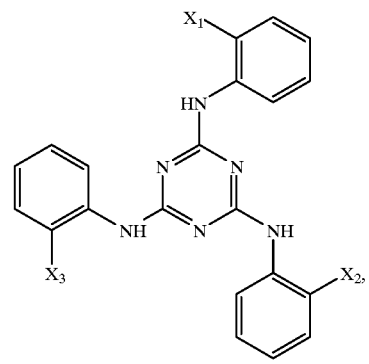

or very particularly triazine compounds of the formula (1), in which $X_1$, $X_2$ and $X_3$ are in the para-position to the phenylamino radical of the triazine, i.e. compounds of the formula (4)

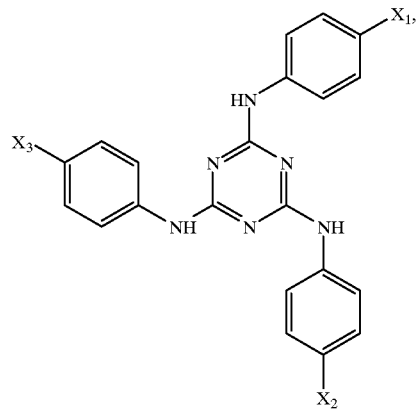

or compounds of formula

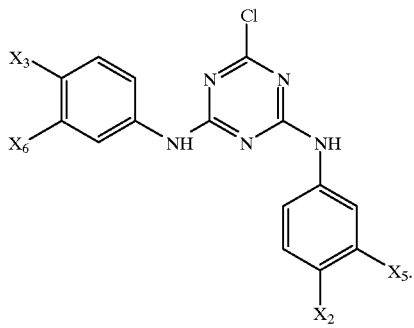

(5)

$X_1$, $X_2$, $X_3$, $X_5$ and $X_6$ are defined as in formula (1).

Triazine compounds of the formula (1) are preferably used, in which $X_1$, $X_2$ and $X_3$ independently of one another are a radical of the formula

and $R_2$ and $R_3$ here are as defined in formula (1).

Among these compounds, in turn those are preferred in which $R_2$ is hydrogen and $R_3$ is a radical of the formula

(3c)

in which $R_7$ is straight-chain or branched $C_1$–$C_{22}$alkyl or a radical of the formula (1b).

Further interesting triazine compounds of the formula (1) are those in which $X_1$ and $X_2$ are a radical of the formula

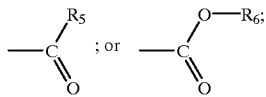

and $X_3$ is a radical of the formula

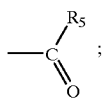

in which $R_5$ and $R_6$ independently of one another are straight-chain or branched $C_1$–$C_8$alkyl.

Triazine compounds of the formula (1) are furthermore preferred in which $X_1$ and $X_2$ independently of one another are a radical of the formula

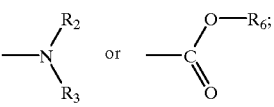

and $X_3$ is a radical of the formula

in which $R_2$ is hydrogen;

$R_3$ is a radical of the formula

(1c)

and $R_1$ and $R_6$ independently of one another are straight-chain or branched $C_1$–$C_8$alkyl.

Triazines of the formula (1) are particularly preferred in which $X_1$, $X_2$ and $X_3$ have the same meaning.

Of predominant interest here are triazine compounds of the formula

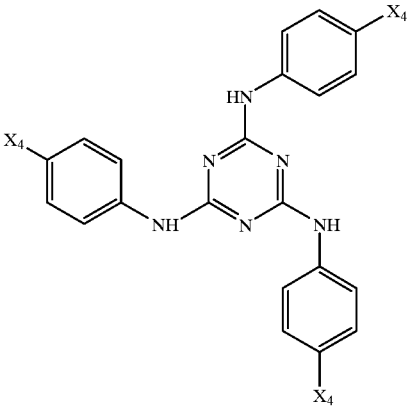

(6)

in which $X_4$ is —CONHR$_8$;

—SO$_2$R$_{10}$; —CN; or

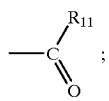

R$_8$ is hydrogen; or straight-chain or branched C$_1$–C$_{22}$alkyl; or a radical of the formula (1b);

R$_9$ is a radical of the formula (6a)

R$_{10}$ is straight-chain or branched C$_1$–C$_{22}$alkyl; or —NH$_2$;

R$_{11}$ is straight-chain or branched C$_1$–C$_{22}$alkyl; or a radical of the formula

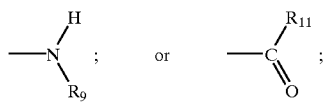

R$_{12}$ is hydrogen; or straight-chain or branched C$_1$–C$_{22}$alkyl; and

A$_2$ is straight-chain or branched C$_1$–C$_8$alkyl.

Very particularly of interest here are compounds of the formula (6), in which

X$_4$ is CONHR$_8$;

in which

R$_8$ is hydrogen; or straight-chain or branched C$_1$–C$_8$alkyl; or a radical of the formula (1b); and R$_9$ and R$_{11}$ are as defined above.

Triazine compounds of the formula (1) are furthermore preferred in which

R$_4$ is branched or straight-chain C$_1$–C$_{22}$alkyl; or

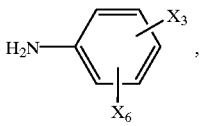

and

R$_2$ and R$_3$ are as defined in formula (1).

Among these triazine compounds, those compounds are very particularly preferred in which R$_2$ is hydrogen and R$_3$ is C$_1$–C$_5$alkyl;

or triazine compounds in which

R$_2$ and R$_3$ are hydrogen.

The triazine compounds of the formula (1) according to the invention are prepared in a manner known per se, for example by reaction of 1 mol of cyanuric chloride with 1 mol in each case of the corresponding aniline compounds of the formula

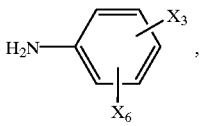

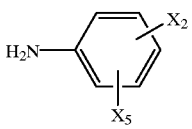

or R—H.

R, X$_2$, X$_3$, X$_5$ and X$_6$ here are as defined in formula (1).

The reaction is usually carried out in a suitable solvent at a temperature from 50 to 200° C.

Suitable solvents here are, for example, acetonitrile, ketones, for example acetone or methyl ethyl ketone; ethers, for example diethyl ether, diisopropyl ether, tetrahydrofuran (THF), dimethylformamide (DMF) or dioxane; aliphatic or aromatic hydrocarbons, for example pentane, heptane, cyclohexane, benzene, toluene, xylene or mixtures thereof; or aliphatic carboxylic acid esters, for example ethyl acetate. The solvent used for the preparation process according to the invention is preferably dimethylformamide (DMF).

The general reaction of trihalotriazine compounds, for example cyanuric fluoride or cyanuric chloride, in which the three halogen atoms are replaced by amino radicals, is known and described in detail in the technical literature, in particular the specialist literature which deals with dyes and optical brighteners.

The triazine compounds of the formula (1) according to the invention are particularly suitable as UV-A filters, i.e. for protecting ultraviolet-sensitive organic materials, in particular the skin and the hair of man and animals, from the harmful action of UV radiation. These compounds are therefore suitable as sunscreens in cosmetic, pharmaceutical and veterinary medicinal preparations. The compounds can be used both in dissolved form and in the micronized state.

The invention therefore further relates to a cosmetic preparation comprising at least one compound of the formula (1), and cosmetically tolerable carriers or adjuncts.

For cosmetic use, the sunscreens according to the invention usually have an average particle size in the range from 0.02 bis 2, preferably 0.05 to 1.5, and very particularly from 0.1 to 1.0μ. The triazine compounds according to the invention, which are usually water-insoluble, can be brought to the desired particle size by customary methods, for example grinding with, for example, a jet, ball, vibration or hammer mill. Preferably, the grinding is carried out in the presence of 0.1 to 30, preferably 0.5 to 15, % by weight, based on the triazine compound employed, of a grinding aid, for example an alkylated vinylpyrrolidone polymer, a vinylpyrrolidone/vinyl acetate copolymer, an acylglutamate or in particular a phospholipid. The nanopigment thus obtained is incorporated in a customary sunscreen recipe. O/W or W/O emulsions are prepared using one or more pigments, also in the presence of one or more oil- or water-soluble UV absorbers, according to known processes for the preparation of sunscreen emulsions.

Besides the triazine compounds according to the invention, the cosmetic preparations can also additionally contain one or more further UV protective substances, for example benzophenones, p-methoxy cinnamates, dibenzoyl-methane derivatives, benzylidene camphor derivatives, p-aminobenzoic acid derivatives, salicylic acid derivatives, diphenyl acrylate derivatives, terephthalydene dicamphor sulfonic acid, menthylanthranilate, $TiO_2$ (differently coated), ZnO, Mica, benzotriazoles, amides containing vinyl groups, or cinnamides. Such protective substances are described, for example, in GB-A-2,286,774 or alternatively are known from Cosmetics & Toiletries (107), 50 et seq. (1992).

The cosmetic preparation according to the invention contains, for example, 0.1 to 15, preferably 0.5 to 10% by weight, based on the total weight of the composition, of a triazine compound of the formula (1) according to the invention or of a mixture of these triazine compounds and a cosmetically tolerable auxiliary.

The cosmetic composition can be prepared by physical mixing of the triazine compound or compounds with the auxiliary by customary methods, for example by simply stirring the individual components together.

The cosmetic preparation according to the invention can be formulated as a water-in-oil or oil-in-water emulsion, as an oil-in-alcohol lotion, as a vesicular dispersion of an ionic or non-ionic amphiphilic lipid, as a gel, solid stick or as an aerosol formulation.

As a water-in-oil or oil-in-water emulsion, the cosmetically tolerable auxiliary preferably contains 5 to 50% of an oil phase, 5 to 20% of an emulsifier and 30 to 90% of water. The oil phase can in this case contain any oil suitable for cosmetic formulations, for example one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

Any conventionally employable emulsifier can be used for the cosmetic formulations according to the invention, for example one or more ethoxylated esters of natural derivatives, such as, for example, polyethoxylated esters of hydrogenated castor oil; or a silicone oil emulsifier, for example silicone polyol, a free or ethoxylated fatty acid soap; an ethoxylated fatty alcohol; a free or ethoxylated sorbitan ester; an ethoxylated fatty acid; or an ethoxylated glyceride.

The cosmetic formulation can also contain further components, for example emollients, emulsion stabilizers, skin humectants, skin bronzing accelerators, thickeners, for example xanthan, moisture retention agents, for example glycerol, preservatives, fragrances and colourants.

The cosmetic formulations according to the invention are distinguished by a high UV absorption and therefore offer very good protection of the human skin against the harmful action of sunlight.

The following examples serve to illustrate the invention.

EXAMPLE 1

45 g (0.3 mol) of p-aminoacetanilide are dissolved in 90 ml of dimethylformamide (DMF) at room temperature. In the course of 1 to 2 minutes, 9.2 g (0.05 mol) of cyanuric chloride are introduced. The reaction proceeds exothermically, the temperature rising to about 60° C. The mixture is stirred further in an oil bath at a bath temperature of 80° C. and concentrated on a rotary evaporator at 100° C. The residue is slowly stirred into 600 ml of water. In this process, the compound of the formula

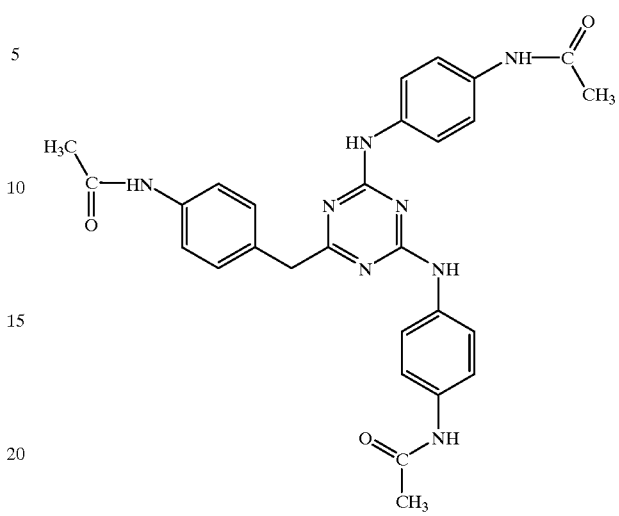

(101)

precipitates in thick flakes.

After filtering off with suction, washing again twice with 30 ml of water in each case and subsequently stirring with acetone, an almost white powder remains.

Yield: 27.9 g (89% of theory);

M.p: 215–218°0 C.;

$\lambda_{max}$: 292 nm (measured in ethanol);

Elemental analysis (calculated for $C_{27}H_{27}N_9O_3[4.5 H_2O]$);

|  | C | H | N | O |
|---|---|---|---|---|
| Calculated: | 51.91 | 5.8 | 20.18 | 22.11 |
| Found: | 51.93 | 5.66 | 20.42 | 21.99 |

EXAMPLE 2

7 g (0.03 mol) of the compound of the formula

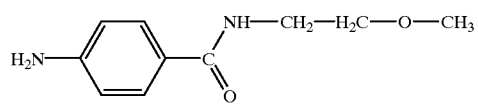

(102a)

are initially introduced into 10 ml of dimethylformamide (DMF). In the course of 1 to 2 minutes, 0.92 g (0.005 mol) of cyanuric chloride is then introduced with vigorous stirring. The mixture is then stirred further at 120° C. for an additional 1.5 hours. After cooling, the reaction mixture is poured into 500 ml of 3% sodium chloride solution, everything initially going into solution and then the precipitate depositing. The mixture is stirred for an additional hour, and the precipitate is filtered off with suction and washed twice with 25 ml of ice water in each case. After drying, 3.44 g of a pale yellow substance remain, being that of the formula

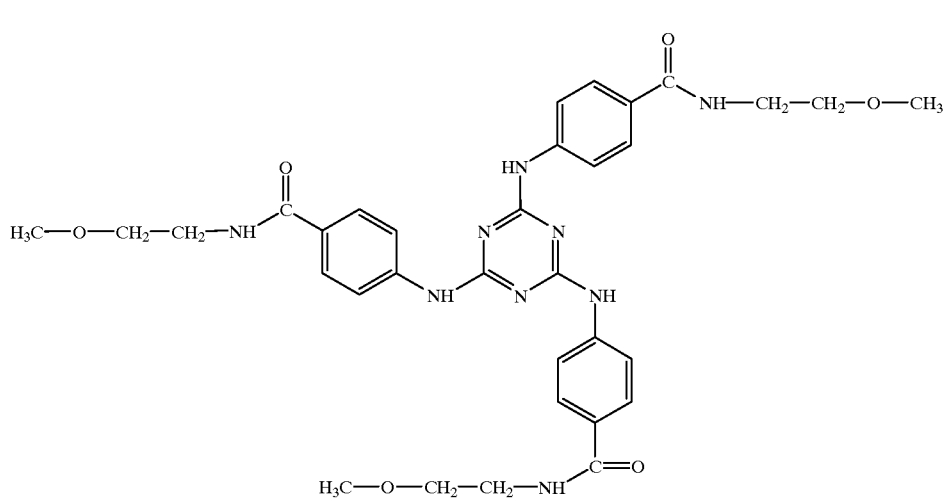
(102)

M.p.: 212–215° C.;
$\lambda_{max}$: 305 nm (measured in ethanol);
Elemental analysis (calculated for $C_{33}H_{39}N_9O_6[3.2\ H_2O]$);

|  | C | H | N | O |
|---|---|---|---|---|
| Calculated: | 55.42 | 6.39 | 17.62 | 20.57 |
| Found: | 55.47 | 6.25 | 17.64 | 20.6 |

EXAMPLE 3

The procedure described in Example 2 is repeated, except that instead of the compound of the formula (102a) 9.8 g (0.06 mol) of p-aminobenzamide are reacted with 1.84 g (0.01 mol) of cyanuric chloride in 30 ml of dimethylformamide (DMF). 3.08 g of a white powder of the formula (103)

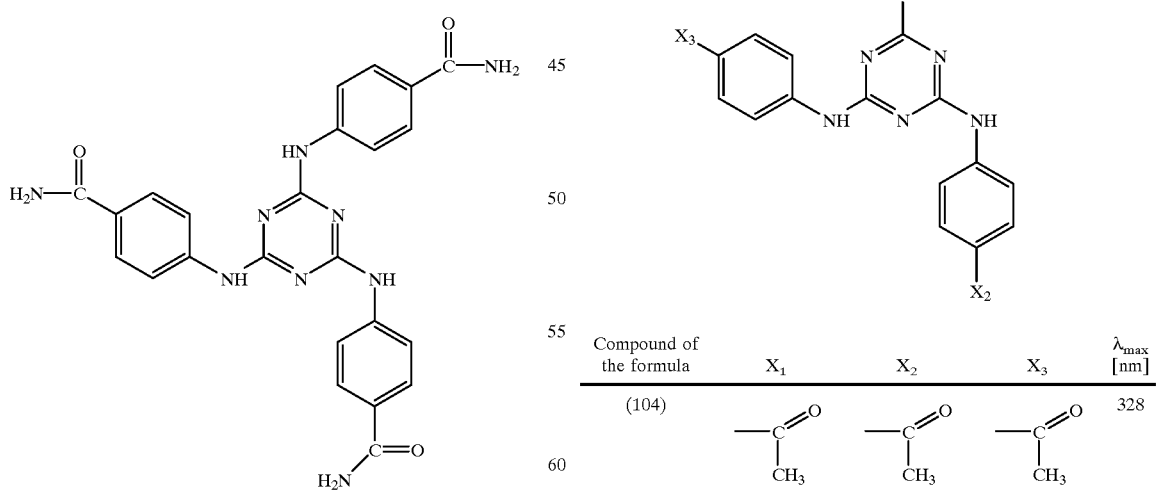

are isolated.
M.p.:>300° C.;
$\lambda_{max}$=305 nm (measured in ethanol).
Elemental analysis (calculated for $C_{24}H_{21}N_9O_3[5.2\ H_2O]$);

|  | C | H | N | O |
|---|---|---|---|---|
| Calculated: | 49.49 | 5.40 | 21.84 | 22.73 |
| Found: | 49.91 | 5.22 | 22.15 | 22.72 |

EXAMPLES 4 TO 9

In accordance with Example 1, compounds of the formulae (104) to (109) can be prepared (Table 1):

TABLE 1

| Compound of the formula | $X_1$ | $X_2$ | $X_3$ | $\lambda_{max}$ [nm] |
|---|---|---|---|---|
| (104) | —C(=O)CH₃ | —C(=O)CH₃ | —C(=O)CH₃ | 328 |
| (105) | —C(=O)O—C₂H₅ | —C(=O)CH₃ | —C(=O)CH₃ | 328 |

TABLE 1-continued

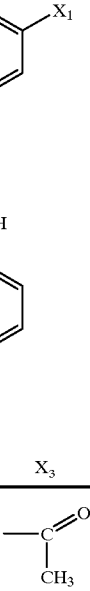

| Compound of the formula | $X_1$ | $X_2$ | $X_3$ | $\lambda_{max}$ [nm] |
|---|---|---|---|---|
| (106) | —SO$_2$NH$_2$ | —SO$_2$NH$_2$ | 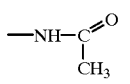 | 330 |
| (107) |  |  | 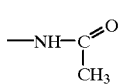 | 305 |
| (108) |  |  | 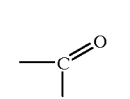 | 305 |
| (109) |  |  | 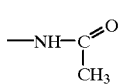 | 330 |

EXAMPLE 10

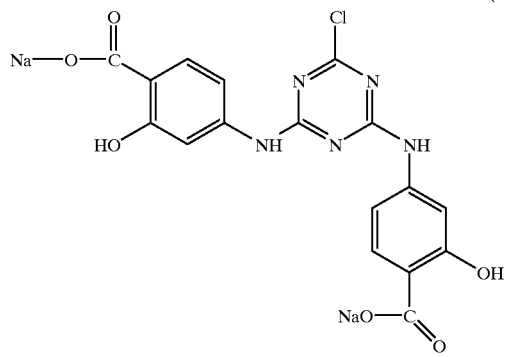

(110)

1.84 g (10 mmol) of cyanuric chloride are dissolved in 20 ml of acetone and the solution is poured onto 20 g of ice. A solution of 4.65 g (22 mmol) of sodium 4-aminosalicylate in 30 ml of water is then added in the course of 20 minutes and the mixture is warmed to 50° C., the pH being kept at 8 using Na$_2$CO$_3$. The reaction is complete after 3 hours. A few undissolved portions of the compound of the formula (110) are filtered from the mixture, and the product is precipitated with sodium chloride, filtered off with suction and washed with saturated sodium chloride solution and a little ice water.

Elemental analysis calculated for $C_{17}H_{10}N_5O_6ClNa_2$ 2 NaCl.3.4 H$_2$O;

|  | C [%] | H [%] | N [%] | Cl (total) [%] | of this Cl$^-$ [%] |
|---|---|---|---|---|---|
| calculated | 31.91 | 2.64 | 10.94 | 16.61 | 11.08 |
| found | 32.16 | 2.68 | 10.92 | 16.60 | 11.24 |

Yield: 5.7 g (8.9 mmol)=89%.

EXAMPLE 11

The compound of the formula

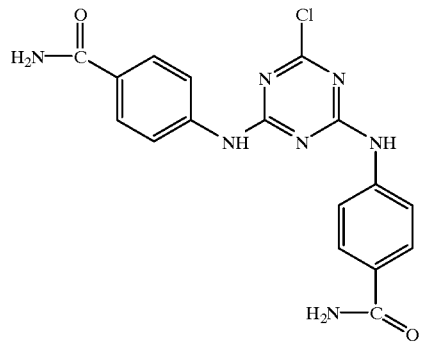

(111)

can be prepared analogously to Example 10.

Elemental analysis calculated for $C_{17}H_{14}N_7O_2Cl$ 0.8 H$_2$O;

|  | C [%] | H [%] | N [%] | Cl [%] | H$_2$O [%] |
|---|---|---|---|---|---|
| calculated | 49.82 | 3.84 | 23.92 | 10.38 | 3.5 |
| found | 50.18 | 4.02 | 23.37 | 10.2 | 3.7 |

Yield: 88%.

EXAMPLE 12

The compound of the formula

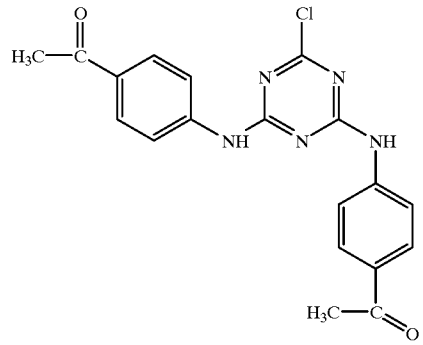

(112)

can be prepared analogously to Example 10.

Elemental analysis calculated for $C_{19}H_{16}N_5ClO_2 \cdot 0.25 H_2O$;

|  | C [%] | H [%] | N [%] | Cl [%] | O [%] |
|---|---|---|---|---|---|
| calculated | 59.07 | 4.3 | 18.12 | 9.1 | 9.41 |
| found | 59.32 | 4.27 | 18.14 | 8.61 | 9.66 |

Yield after recrystallizing from dioxane/water: 52%.

The compounds of the formulae (110) to (112) are starting compounds for the preparation of unsymmetrical triazine UV absorbers. They can be reacted with p-aminosalicylic acid, p-aminobenzamide, p-aminoacetophenone or p-aminoacetanilide in methylcellosolve at 130° C. to give the desired compounds.

However, they can also be reacted with aliphatic amines or alcohols, e.g. to give compounds of the formula (113)

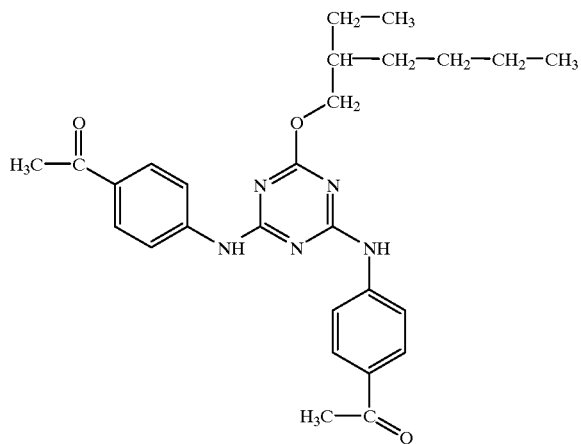

M.p.: 231–232;
$\lambda_{max}$=323 nm.
or with ethylene glycol to give the Compound of the formula (114)

M.p.=220–222° C.;
$\lambda_{max}$=322 nm.

EXAMPLE 13

After grinding in water with quartz sand and with the aid of 8% phospholipid (Phospholipon 80) as an aid, the compound of the formula (101) is ground to an average particle size of 250 nm. The nanopigment suspension thus obtained is incorporated in the following recipe:

Composition:

| Phase A: | |
|---|---|
| Dimethicone | 2% |
| Isopropyl myristate | 9% |
| Stearyl alcohol | 10% |
| Stearic acid | 4% |
| Octyl methoxycinnamate | 3.5% |
| Phase B: | |
| Triethanolamine | 1.2% |
| Carbomer 934 (1%) | 5.0% |
| 50% suspension of the compound of the formula (101) | 9.6% (4.8% active compound) |
| $H_2O$ | 55.7% |

Phase A is separately homogenized very carefully and, like phase B, separately warmed to 75–80° C. Phase B is then added to phase A with vigorous stirring. The mixture is allowed to cool with stirring.

The light protection factor of this sun cream is 15.5 (determined using the SPF analyzer SPF 290 from Optometrics).

EXAMPLE 14

The compound of the formula (101) is ground to an average particle size of 180 nm in water using "zirconium sand" and with addition of 7% Plantaren 2000. The nanopigment suspension thus obtained is incorporated in the following recipe:

Composition:

| Phase A: | |
|---|---|
| Ceteareth-6 (and) stearyl alcohol | 2% |
| Ceteareth-25 | 2% |
| Cetearyl alcohol | 5% |
| Caprylic/capric triglyceride | 5% |
| Cetearyl octanoate | 10% |
| Petroleum jelly | 5% |
| Phase B: | |
| Propylene glycol | 3.0% |
| Carbopol 934 | 0.2% |
| 50% suspension of the compound of the formula (101) | 5.0% (based on the active compound content) |
| $H_2O$ | 57.53% |
| Phase C: | |
| Triethanolamine | 0.27% |

Phases A and B are warmed to 75–80° C. Phase B is then added to phase A with thorough homogenization. This is then followed by phase C and the mixture is intensively homogenized.

The SPF of this O/W emulsion is 9.5 (determined using the SPF analyzer 290 from Optometrics).

What is claimed is:

1. A cosmetic preparation, comprising at least one triazine compound of the formula

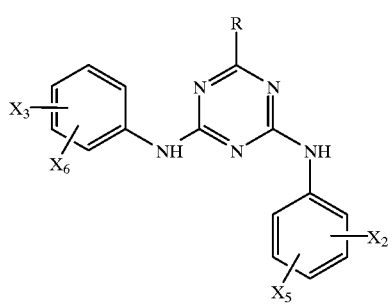

(1)

in which
R is halogen; straight-chain or branched $C_1$–$C_{22}$-alkyl; straight-chain or branched $C_1$–$C_{22}$-alkoxy; straight-chain or branched $C_1$–$C_{22}$-hydroxyalkoxy; straight-chain or branched $C_1$–$C_{22}$-alkoxyalkyl; —$NHR_1$;

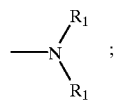

or a radical of the formula

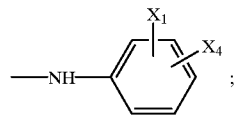

(1a)

$X_1$, $X_2$ and $X_3$ independently of one another are —$CONHR_1$;

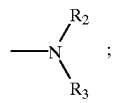

—$SO_2R_4$; —CN;

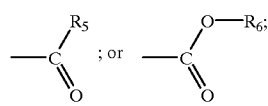

$R_1$ is hydrogen; straight-chain or branched $C_1$–$C_{22}$alkyl; $C_6$–$C_{12}$aryl which is unsubstituted, monosubstituted or polysubstituted by $C_1$–$C_4$alkyl; $C_7$–$C_{10}$aralkyl which is unsubstituted, monosubstituted or polysubstituted by $C_1$–$C_4$alkyl; $C_5$–$C_8$cycloalkyl; or a radical of the formula

(1b)

in which
$A_1$ is straight-chain or branched $C_1$–$C_8$alkyl; $C_5$–$C_8$-cycloalkyl; $C_6$–$C_{12}$aryl which is unsubstituted, monosubstituted or polysubstituted by $C_1$–$C_4$alkyl; $C_7$–$C_{10}$aralkyl which is unsubstituted, monosubstituted or polysubstituted by $C_1$–$C_4$alkyl; and $m_1$ is 1 to 10;

$R_2$ and $R_3$ independently of one another are hydrogen; straight-chain or branched $C_1$–$C_{22}$alkyl; $C_5$–$C_8$cycloalkyl; $C_6$–$C_{12}$aryl which is unsubstituted, monosubstituted or polysubstituted by $C_1$–$C_4$alkyl; $C_7$–$C_{10}$aralkyl which is unsubstituted, monosubstituted or polysubstituted by $C_1$–$C_4$alkyl; a radical of the formula (1b); or a radical of the formula

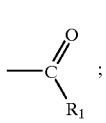

(1c)

$R_4$ is branched or straight-chain $C_1$–$C_{22}$alkyl; $C_5$–$C_8$cycloalkyl; $C_6$–$C_{12}$aryl which is unsubstituted, monosubstituted or polysubstituted by $C_1$–$C_4$alkyl; $C_7$–$C_{10}$aralkyl which is unsubstituted, monosubstituted or polysubstituted by $C_1$–$C_4$alkyl; a radical of the formula (1b); or

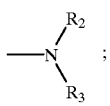

$R_5$ and $R_6$ independently of one another are hydrogen; straight-chain or branched $C_1$–$C_{22}$alkyl; $C_5$–$C_8$cycloalkyl; $C_6$–$C_{12}$aryl which is unsubstituted, monosubstituted or polysubstituted by $C_1$–$C_4$alkyl; $C_7$–$C_{10}$aralkyl which is unsubstituted, monosubstituted or polysubstituted by $C_1$–$C_4$alkyl; or a radical of the formula (1b);

$X_4$, $X_5$ and $X_6$ are hydrogen; or hydroxy;

where compounds of the formula (1) are not additionally included in which
$X_1$ and $X_2$ are —$CONHR_1$; and $X_3$ is then

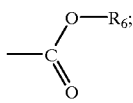

or compounds in which
$X_1$ and $X_2$ are

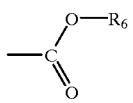

and $X_3$ is —CONHR$_1$; or compounds in which
$X_1$, $X_2$ and $X_3$ are

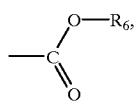

and a cosmetically tolerable carrier or adjunct.

2. A cosmetic preparation according to claim 1, wherein "alkylene" in formula (1b) is an alkylene group which has 2 to 4 carbon atoms.

3. A cosmetic preparation according to claim 2, wherein the alkylene group is a bivalent radical of the formula —CH$_2$—CH$_2$—; —CH$_2$CH$_2$CH$_2$—; —CH$_2$—CH$_2$—CH$_2$—CH$_2$—;

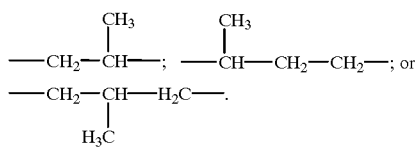

4. A cosmetic preparation according to claim 1, wherein the triazine compound is of the formula

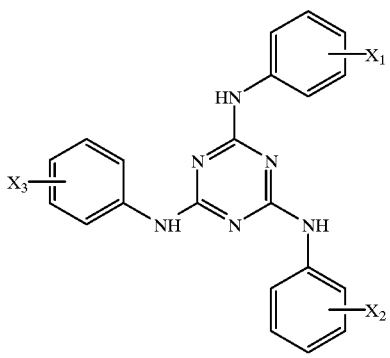

(2)

wherein $X_1$, $X_2$ and $X_3$ are defined as in claim 1.

5. A cosmetic preparation according to claim 1, wherein the triazine compound is of the formula

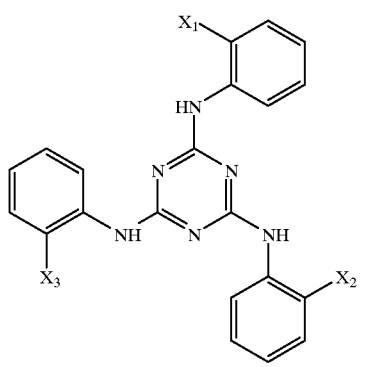

(3)

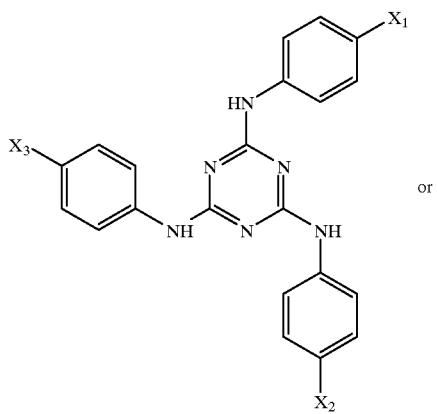

(4)

or

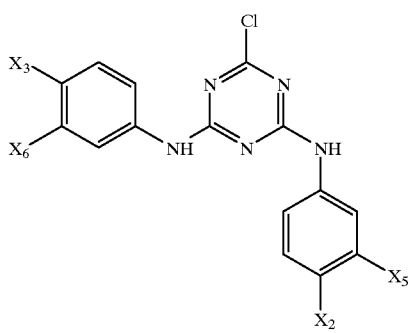

(5)

in which $X_1$, $X_2$, $X_3$, $X_5$ and $X_6$ are defined as in claim 1.

6. A triazine compound according to claim 1, wherein $X_1$, $X_2$ and $X_3$ independently of one another are a radical of the formula

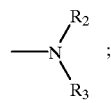

and $R_2$ and $R_3$ are as defined in claim 1.

7. A cosmetic preparation according to claim 6, wherein $R_2$ is hydrogen and $R_3$ is a radical of the formula

(3c)

in which $R_7$ is straight-chain or branched C$_1$–C$_{22}$alkyl or a radical of the formula (1b).

8. A cosmetic preparation according to claim 1, wherein $X_1$ and $X_2$ are a radical of the formula

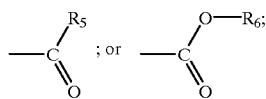

and $X_3$ is a radical of the formula

in which $R_5$ and $R_6$ independently of one another are straight-chain or branched $C_1$–$C_8$alkyl.

9. A cosmetic preparation according to claim 1 wherein $X_1$ and $X_2$ independently of one another are a radical of the formula

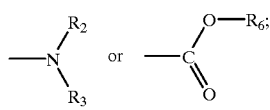

and $X_3$ is a radical of the formula

in which $R_2$ is hydrogen;

$R_3$ is a radical of the formula

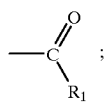

(1c)

and $R_1$ and $R_6$ independently of one another are straight-chain or branched $C_1$–$C_8$alkyl.

10. A cosmetic preparation according to claim 1, wherein $X_1$, $X_2$ and $X_3$ have the same meaning.

11. A cosmetic preparation according to claim 10, wherein the triazine compound is of the formula

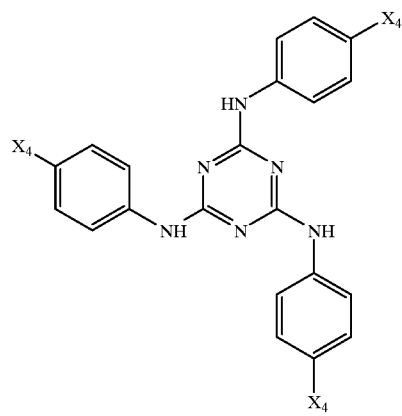

(6)

in which $X_4$ is —$CONHR_8$;

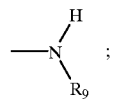

—$SO_2R_{10}$; —CN; or

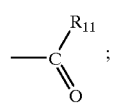

$R_8$ is hydrogen; or straight-chain or branched $C_1$–$C_{22}$alkyl; or a radical of the formula (1b);

$R_9$ is a radical of the formula

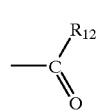

(6a)

$R_{10}$ is straight-chain or branched $C_1$–$C_{22}$alkyl; or —$NH_2$;

$R_{11}$ is straight-chain or branched $C_1$–$C_{22}$alkyl; or a radical of the formula —(alkylene-O)–$A_2$   (6b)

$R_{12}$ is hydrogen; or straight-chain or branched $C_1$–$C_{22}$alkyl; and $A_2$ is straight-chain or branched $C_1$–$C_8$alkyl.

12. A cosmetic preparation according to claim 11, wherein $X_4$ is $CONHR_8$;

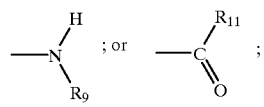

in which $R_8$ is hydrogen; or straight-chain or branched $C_1$–$C_8$alkyl; or a radical of the formula (1b); and $R_9$ and $R_{11}$ are as defined in claim 11.

13. A method of protecting human and animal hair and skin from the harmful action of UV radiation, which comprises applying to the hair or skin a cosmetic preparation comprising a protectively effective amount of a triazine compound as defined in claim 1.

14. A preparation according to claim 1, which contains further UV protective substances.

15. A preparation according to claim 14, which as further UV protective substances contains benzophenones, p-methoxy cinnamates, dibenzoylmethane derivatives, benzylidene camphor derivatives, p-aminobenzoic acid derivatives, salicylic acid derivatives, diphenyl acrylate derivatives, terephthalydene dicamphor sulfonic acid, menthylanthranilate, $TiO_2$ (differently coated), ZnO, Mica, benzotriazoles, amides containing vinyl groups, or cinnamides.

* * * * *